United States Patent [19]

Ikenaka et al.

[11] Patent Number: 4,697,006

[45] Date of Patent: Sep. 29, 1987

[54] MODIFIED OLIGOSACCHARIDES USED AS SUBSTRATE FOR MEASURING α-AMYLASE ACTIVITY

[75] Inventors: Tokuji Ikenaka, Sakai; Kaoru Omichi, Toyonaka, both of Japan

[73] Assignee: Wako Pure Chemical Industries, Ltd., Osaka, Japan

[21] Appl. No.: 907,358

[22] Filed: Sep. 15, 1986

Related U.S. Application Data

[62] Division of Ser. No. 532,099, Sep. 14, 1983, Pat. No. 4,622,295.

[30] Foreign Application Priority Data

Sep. 16, 1982 [JP] Japan ............................. 57-161457
Jul. 28, 1983 [JP] Japan ............................. 58-138344

[51] Int. Cl.$^4$ ..................... C08B 37/00; C12Q 1/40; C12Q 1/54; C12N 9/26
[52] U.S. Cl. ................................. 536/17.2; 536/1.1; 536/17.3; 536/4.1; 536/18.7; 536/17.9
[58] Field of Search ................ 536/1.1, 17.2, 17.3, 536/4.1, 18.7, 17.9

[56] References Cited

U.S. PATENT DOCUMENTS 4,233,403  11/1983  Menson et al. .................... 435/22
4,544,631  10/1985  Rauscher et al. .................. 435/22

FOREIGN PATENT DOCUMENTS 3000292  7/1981  Fed. Rep. of Germany ........ 435/22
58-71897  4/1983  Japan ................................... 435/22

OTHER PUBLICATIONS

Wilkinson, J. H., *The Principles and Practice of Diagnostic Enzymology*, (An Edward Arnold Publication), pp. 149–154, 1976.
Chem. Abstr. 82, 151408h (1975).
Chem. Abstr. 87, 98151u (1977).
Chem. Abstr. 90, 182383r (1979).
Chem. Abstr. 91, 119572g (1979).
Chem. Abstr. 88, 148201d (1978).

*Primary Examiner*—Ronald W. Griffin
*Attorney, Agent, or Firm*—Armstrong, Nikaido, Marmelstein & Kubovcik

[57] ABSTRACT

A modified oligosaccharide having at most 7 glucose units and having a substituent selected from the group consisting of 2-aminopyridyl, 3-aminopyridyl, anilino, methylanilino, hydroxyanilino, carboxyphenylamino and hydroxyl groups at at least one end moiety of said oligosaccharide is suitable as substrate for measuring α-amylase activity or for measuring α-amylase isozymes.

4 Claims, 5 Drawing Figures

MODIFIED OLIGOSACCHARIDES USED AS SUBSTRATE FOR MEASURING α-AMYLASE ACTIVITY

This is a division of application Ser. No. 532,099 filed Sept. 14, 1983, now U.S. Pat. No. 4,622,295, issued Nov. 1, 1986.

This invention relates to modified oligosaccharides used as substrate for measuring α-amylase activity or as substrate for measuring α-amylase isozymes, a method for measuring α-amylase activity using such a substrate and a method for measuring α-amylase isozymes using such substrates.

Measurement of α-amylase activity in a sample, particularly in saliva, pancreatic juice, blood and urine in human living body is important for diagnosis in medical science. For example, α-amylase activity in blood and urine shows a remarkable increase in the case of pancreatitis, cancer of the pancreas, and parotitis compared with normal values.

Various processes for measuring α-amylase activity have been proposed and can be divided into three groups, that is, an amyloclastic method, a chromogenic method, and a saccharogenic method.

As to the amyloclastic method, the Caraway method has been most widely used, but there are some problems in that reproducibility is not good due to inhibition of coloring of starch by iodine by co-existing protein or due to short reaction time.

As to the chromogenic method, the blue starch method is generally used, wherein there is used an insoluble substrate obtained by combining starch or amylose with a dyestuff and a soluble dyestuff produced by an enzymatic reaction is measured. This method is widely used recently, but there are many problems in that the activity as substrate is weak, the reaction system is ununiform due to insolubility, complicated procedures are necessary and application to auto analyzers is difficult, etc.

As to the saccharogenic method, the Somogyi method is typical one, but there are problems in that since the measured value includes the value of glucose present in a sample and the blank value of sample should also be measured, the procedures are undesirably complicated, etc.

As mentioned above, individual methods for measuring α-amylase activity have specific defects. In addition, there are defects common to the above-mentioned methods in that variations in measured values are produced depending on the quality of starch used as substrate, and the α-amylase reaction cannot be measured as a true kinetic reaction.

Starch is, as well known, a mixture of amylose which is a linear glucan jointed by α-1,4-links and amylopectin which is a branched glucan having branches joined by α-1,6-links. Since the mixing ratio of amylose and amylopectin, molecular weight, degree of branching, structure of branching are changed depending on the kinds of raw plants, harvest-time, growing districts, etc., starch is an ununiform mixture.

When ununiform starch is used as substrate, a kinetic reaction cannot be obtained, and thus kinetics of α-amylase cannot be detected.

Kinetic detection of α-amylase has been conducted by using an oligosaccharide having 4 to 7 glucose units.

Recently, there are proposed methods for using as substrate uniform substances having a distinct structure in place of starch, for example, oligosaccharides such as maltotetraose, maltopentaose, maltohexaose, maltoheptaose, etc. (Chem. Abstr. 82, 151408h (1975), ibid. 88, 148201d (1978)), an oligosaccharide having a reducing end bonded with a chromogen such as p-nitrophenol, etc. (Chem. Abstr. 90, 182383r (1979)).

In these methods, it is necessary to use as coupling enzyme α-glucosidase (E.C. 3.2.1.20, α-D-glucoside glucohydrolase) or glucoamylase (E.C. 3.2.1.3,1,4-α-D-glucan glucohydrolase). These coupling enzymes are exo type enzymes which hydrolyze an α-1,4-glucoside bond from a non-reducing end of saccharide chain having α-1,4-glucoside bonds irrespective of the α-amylase reaction to decompose the substrate. Therefore, a reagent solution for measurement becomes unstable, and reagent blank values become remarkably high, which results in making measuring accuracy remarkable worse. Further, since a sufficient amount of glucoamylase or α-glucosidase necessary for the measurement cannot be used, it is difficult to construct the measuring method with high accuracy. Thus, the removal of such defects is desired.

On the other hand, to measure α-amylase activity, for example α-amylase in blood, by dividing into α-amylase isozymes is important for analyzing hyperamylasemia and elucidating the conditions of disease and is applied to daily clinical examinations.

There have been proposed various methods for separating α-amylase isozymes, for example, (1) separation by use of difference in charge, (2) a gel filtration method, (3) an affinity chromatographic method, (4) an immunological method, (5) a method by use of α-amylase inhibitors, etc. Among these methods, the method (1) wherein the separation by use of difference in charge is conducted by electrophoresis and the method (5) by the use of α-amylase inhibitors are practically applied to clinical examinations.

In the electrophoresis methods, suitable ones for clinical examinations are those using a cellulose acetate film or a thin layer of polyacrylamide gel. But there are defects in that measuring procedures are complicated and it requires a long time for the measurement.

The method (5) using α-amylase inhibitors is a method using properties of an amylase inhibitor derived from wheat in that said inhibitor strongly inhibits α-amylase derived from salivary glands than α-amylase derived from pancreas, and calculating the proportions of the two. But presently, since no inhibitor is found to completely specifically inhibit α-amylase derived from either pancreas or salivary glands, there is employed a method wherein an activity ratio of α-amylase derived from pancreas and salivary glands in a sample is determined from a calibration curve prepared by using enzyme standard solutions containing known amounts. Said method can be conducted with relatively simple procedures and is used widely recently. But according to said method, in order to obtain the activity ratio of α-amylase derived from pancreas and that derived from salivary glands, it is necessary to conduct the measuring two times with the use of inhibitor and without the use of inhibitor, which makes the procedure still complicated. Thus, an improvement of such a method is desired.

Objects of this invention are to provide modified oligosaccharides used as substrate for measuring α-amylase activity or as substrate for measuring α-amylase isozymes and a process for using such modified oligasaccharides as substrate for measuring α-amylase activity or for measuring α-amylase isozymes.

This invention provides a modified oligosaccharide havng at most 7 glucose units and having a group selected from the group consisting of 2-aminopyridyl, 3-aminopyridyl, anilino, methylanilino, hydroxyanilino, carboxyphenylamino and hydroxyl groups at at least one end moiety of said oligosaccharide usable as substrate for measuring α-amylase activity or for measuring α-amylase isozymes.

This invention also provides a process for using such a modified oligosaccharide as substrate for measuring α-amylase activity or for measuring α-amylase isozymes.

This invention also provides a process for measuring α-amylase activity by using such a modified oligosaccharide as substrate.

This invention still further provide a process for measuring α-amylase isozymes by using such modified oligosaccharides as substrate.

In the attached drawings.

In the case of measuring α-amylase activity, it is preferable to use as modified oligosaccharide a compound of the formula:

(I)

wherein $R_1$ is a 2-aminopyridyl group, 3-aminopyridyl group, an anilino group, a methylanilino group, a hydroxyanilino group or a carboxyphenylamino group; and n is an integer of 2 to 5.

The modified oligosaccharide of the formula (I) has an excellent affinity to α-amylase and is a good substrate for α-amylase but is not a substrate for glucoamylase or α-glucosidase. Further, a product obrained by the action of α-amylase has a group of the formula: —CH₂NHR, wherein R is a residue obtained by removing —NH— from $R_1$, which is able to be detected spectrophotometrically.

The modified oligosaccharide of the formula (I) can be produced as follows.

Using dextrin as a starting material, the primary alcohol moiety of a glucose unit of dextrin is partially oxidized with dimethylsufoxide and N,N'-dicyclohexylcarbodiimide. For example one glucose unit per about 30 glucose units is oxidized. This reaction can be conducted according to the process of G. H. Jones disclosed in Method in Carbohydrate Chemistry, vol. VI, pp. 315–322 (1972) published by Academic Press, New York.

The oxidation reaction is stopped by the addition of oxalic acid. Then, an organic amine having a group giving $R_1$ such as 2-aminopyridine, etc. is added to form a Schiff's base and sodium cyanoborohydride is added to the reaction system and heated at 95° C. for about 20 minutes to proceed the reaction. Water is added to the reaction mixture and a precipitate produced is removed by filtration. To the filtrate, hydrochloric acid is added to make the pH about 1.0 and after the decomposition of sodium cyanoborohydride the pH is changed to neutral. The resulting solution is subjected to gel filtration using a column packed with Biogel P-2 and high molecular fractions (modified dextrin) are collected.

To the modified dextrin, liquefying type α-amylase derived from *Bacilluls subtilis* is added and reacted in a buffer solution of pH about 5.5 at 37° C. for about 30 minutes. Then, the reaction solution is heated at 70° C. or higher for 20 to 60 minutes to inactivate α-amylase. After heat treatment, the reaction solution is cooled to about 20° C. and pH of the reaction solution is adjusted to pH 6 to 8. Then, α-glucosidase or glucoamylase is added to the resulting solution and incubated at 37° C. for 20 to 50 hours to give modified oligosaccharide by the action of α-glucosidase or glucoamylase.

This reaction can be generarized and represented by the following equation:

In the above equation, G is a glucose unit: X is a group represented by the formula: —CH₂R₁ such as and l, m, and n are independently zero or an integer of 1 or more.

In the next place, the resulting mixture is condensed and subjected to column chromatography using a column packed with Biogel P-4 to give individual fractions of modified oligosaccharides having the $R_1$ group such as aminopyridyl groups, etc. at non-reducing end glucose unit, for example, modified maltotetraose, modified maltopentaose, modified maltohexaose, and modified maltoheptaose.

A series of reactions mentioned above can be summarized as follows: Several primary alcohol groups (—CH₂OH) of dextrin are oxidized to aldehyde groups (—CHO), which are changed to a Schiff's base by the action of an organic amine such as 2-aminopyridine having the $R_1$ groups as defined above, followed by reduction to give modified dextrin. Then, by enzymatic hydrolysis, the desired modified oligosaccharides can be obtained.

In the preparation of the modified oligosaccharide of the formula (I), as polysaccharide which is a starting material, there can be used any sugar of long chain having α-1,4-glycoside bonds therein, such as starch, amylose and the like other than dextrin.

Further, in the step of obtaining a modified polysaccharide from an oxidized polysaccharide, there can be used any organic amines, other than 2-aminopyridine, having an amino group which can form a Schiff's base with the aldehyde group of the oxidized polysaccharide. Examples of such organic amines are 2-aminopyridine, 3-aminopyridine, aniline, 2-hydroxyaniline, aminobenzoic acid, methylaniline, etc. In this case, the finally obtained modified oligosaccharide is an oligosaccharide modified by the corresponding modifying group. That is, 2-aminopyridine or 3-aminopyridine gives an aminopyridine modified oligosaccharide, aniline gives an aniline modified oligosaccharide, 2-hydroxyaniline or the like gives a hydroxyaniline modified oligosaccharide, aminobenzoic acid gives an aminobenzoate modified oligosaccharide, and methylaniline or the like gives an alkylaniline modified oligosaccharide.

α-Amylase used for hydrolyzing the modified dextrin to modified oligosaccharides may be any kind and not limited to a special kind. For example, amylases derived from pancreas of animals and from microorganisms can be used. The above-mentioned liquefying type α-amylase derived from *Bacillus subtilis* can effectively be used, since the reaction is stopped or retarded at the state of oligosaccharide having about 10 glucose units and the control of reaction product is easy.

By using the modified oligosaccharide of the formula (I) as substrate, α-amylase activity can be measured by, for example, a high performance liquid chromatographic method (HPLC) or a spectrophotometric method as follows.

(1)

HIGH PERFORMANCE LIQUID CHROMATOGRAPHIC (HPLC) METHOD

This method is based on the properties that an aminopyridyl group emits fluorescence (excitation wavelength 320 nm, fluorescence wavelength 400 nm) or UV absorption (at 310 nm). After the α-amylase reaction using for instance the modified maltohexaose as substrate, the resulting solution containing a produced modified oligosaccharide having two or three glucose units therein and having the aminopyridyl group at a non-reducing terminal glucose unit is subjected to HPLC. α-Amylase activity can be obtained by comparing an effluent peak of the resulting solution with an effluent peak of standard solution having a known activity value.

In the HPLC, the column and the eluate are not limited particularly. As the column, there can be used TSK-Gel LS 410, 5 μm, C 18 (available from Toyo Soda Manufacturing Co., Ltd.). As the eluate, there can be used effectivey 0.1M acetic acid containing 0.1% n-butanol.

The α-amylase activity measuring method by using as substrate the modified oligosaccharide of the formula (I) and analysis by HPLC method has the following advantages (a) to (e) and it becomes possible to establish various combinations of measuring steps applying the advantages of (a) to (e).

(a) The modified oligosaccharide is easily soluble in water and has high reactivity with α-amylase.

(b) Since a single compound is used as a substrate, a stoichiometric reaction is attained and kinetics of α-amylase can be detected.

(c) Since no coupling enzyme is used after the α-amylase reaction, it is easy to detect kinetics of α-amylase.

(d) Since the produced oligosaccharide having two or three glucose units and the aminopyridyl or the like modifying group is separated and then subjected to measuring, there is no influence of glucose already present in a blood sample.

(e) Since the detection is conducted by a fluorophotometric method, high sensitive measuring is possible and thus a very small amount of sample can be used for the measuring.

(2)

SPECTROPHOTOMETRIC METHOD

Since glucoamylase or α-glucosidase is an exo type enzyme, the modified oligosaccharide of the formula (I) cannot be used as substrate. In contrast, since α-amylase is an endo type enzyme which hydrolyzes any α-1,4-glycoside bonds of oligosaccharide, the modified oligosaccharide of the formula (I) can be used as substrate. By the enzymatic action of α-amylase, the modified oligosaccharide is hydrolyzed to form newly a non-reducing end. To the newly formed non-reducing end, α-glucosidase or glucomylase acts to form glucose, the amount of which is measured to determine α-amylase activity.

There have been known various methods for quantitatively determining glucose, which methods can be used in this invention. Major methods for quantitatively determining glucose are shown below.

One methiod is as follows. When glucose is acted by glucose oxidase, it is oxidized to produce hydrogen peroxide. The produced hydrogen perioxide oxidizes a chromogen quantitatively by means of peroxidase present to give an oxidized chromogen. The amount of glucose in the reaction solution can be measured by colorimetric determination of the color produced by the oxidized chromogen. These reactions can be shown below.

(2)

(3)

GOD: glucose oxidase
POD: peroxidase

Another method is as follows. Glucose is changed to glucose-6-phosphate in the presence of ATP by hexokinase. The produced glucose-6-phosphate is changed to gluconolactone-6-phosphate in the presence of NAD by glucose-6-phosphate dehydrogenase. On the other hand, NAD is reduced to NADH. By measuring an increase in absorbance of NADH at near 340 nm, the amount of glucose in the reaction solution can be determined. These reactions can be shown below.

(4)

(5)

gluconolactone-6-phosphate + NADH

ATP: adenosine triphosphate
ADP: adenosine diphosphate
NAD: nicotinamide adenine dinucleotide
NADH: nicotinamide adenine dinucleotide, reduced form
G-6-PDH: glucose-6-phosphate dehydrogenase.

In the spectrophotometric method wherein a sample is treated with α-amylase and simultlaneously or successively with a coupling enzyme such as glucoamylase or α-glucosidase using the modified oligosaccharide as substrate and glucose produced is determined quantitatively, there is a possibility of influence of glucose present in a sample, particularly in a living sample such as serum, urine, etc. It is an effective means to remove or extinguish the glucose present in a sample before the α-amylase reaction in practicing the process of this invention.

As to the removing or extinguishing method of glucose in the sample, there can be used a method of using glucose oxidase-catalase, a method of using hexokinase [Japanese Patent Appln Kokai (Laid-Open) No. 47495/82)], a method of using glucose oxidase-peroxidase, and the like, alone or in combination of these methods.

It is also possible to measure α-amylase activity by measuring maltose produced by the action of α-amylase using the modified oligosaccharide of the formula (I) as substrate. The measuring of maltose is disclosed in, for example, Chem. Abstr. 87, 98151lu (1977) (U.S. Pat. No. 4,036,697).

The α-amylase activity measuring method by using as substrate the modified oligosaccharide of the formula (I) and analysis by spectrophotometric method has the following advantages (a) to (f) and it becomes possible to establish various combinations of measuring steps applying the advantages of (a) to (f).

(a) The modified oligosaccharide is easily soluble in water and has high reactivity with α-amylase.

(b) Since a single compound is used as a substrate, a stoichiometric reaction is attained and kinetics of α-amylase can be detected.

(c) Since the modified oligosaccharide is a specific substrate for α-amylase but is not a substrate for glucoamylase or α-glucosidase, there takes place no side reaction and reagent blank values are remarkably small.

(d) Since a sufficient amount of glucoamylase or α-glucosidase can be used, the reaction after the α-amylase reaction is fast and accurate rate assay is possible.

(e) Reagent solutions for measuring are stable.

(f) Application to autoanalyzers is possible.

The measuring of α-amylase activity by using the modified oligosaccharide of the formula (I) as substrate is illustrated by way of the following Examples.

EXAMPLE 1

Preparation of Modified Oligosaccharide

In 250 ml of dimethylsulfoxide, 10 g of dextrin and 15 g of N,N'-dicyclohexylcarbodiimide were dissolved. To the resulting mixture, a mixed solution of 1 ml of dichloroacetic acid and 12.5 ml of dimethylsulfoxide was added, mixed well and reacted at 20°-25° C. for 40 minutes. To the reaction solution, a solution obtained by dissolving 6.3 g of oxalic acid dihydrate in 25 ml of methanol was added to stop the reaction. To the resulting reaction mixture, a 2-aminopyridine solution (a solution obtained by mixing 60 g of 2-aminopyridine, 90 ml of water, 24 ml of acetic acid and 24 g of sodium cyanoborohydride) was added and heated at 95° C. for 20 minutes. After the reaction with heating, 1 liter of water was added to give a precipitate, which was filtered. The filtrate was made pH 1.0 with 6N HCl. After the decomposition of excess sodium cyanoborohydrodide, the resulting solution was adjusted pH 7.0 with 6N ammonium hydroxide and condensed in vacuum. A part of the condensate in an amount of 350 mg was dissolved in water and subjected to gel filtration. As the column, there was used one having a diameter of 2.6 cm and a height of 113 cm packed with Biogel P-2 equilibrated with 10 mM ammonium bicarbonate (available from Bio Rad Lab.). This column procedure was repeated twice (the charging amount of the condensate was each 350 mg), followed by collection of high molecular fractions and freeze-drying. The yield was about 700 mg and the degree of modification was 3.1% based on glucose unit from the absorbance at 310 nm in 0.1M acetic acid. The degree of modification was measured according to the method of S. Hase et al (J. Biochem., 85, 217 (1979)).

In 15 ml of water, 470 mg of the resulting modified dextrin was dissolved and mixed with 90 ml of a 30 mM sodium acetate buffer containing 3 mM calcium acetate buffer (pH 5.5). To the resulting mixture, 50 units of liquefying type α-amylase derived from Bacillus subtilis was added and incubated at 37° C. for 25 minutes. After inactivating the α-amylase by heating at 100° C. for 15 minutes, 150 units of glucoamylase was added to the resulting mixture and incubated at 37° C. for 24 hours, followed by addition of 150 units of glucoamylase and the incubation for 24 hours.

The hydrolyzed products were condensed and subjected to column chromatography using a column having a diameter of 1.9 cm and a height of 212 cm packed with Biogel P-4 equilibrated with 20 mM acetic acid (available from Bio Rad Lab.).

Each fraction of modified oligosaccharides having 4 to 7 glucose units was collected and subjected to freeze-drying.

Purification of each modified oligosaccharide was carried out by HPLC using a large column (7×300 mm) packed with TSK-Gel LS 410, 5 μm, C~and 0.1M ammonium acetate buffer solution containing 0.045% n-butanol (pH 3.9) as eluate with a flow rate of 3.0 ml/min.

Identification of Structure

To a mixture of 30 μl of the sample, 100 μl of 0.3% sodium borohydride in water was added. After standing for 3 hours at room temperature, 50 μl of 2M acetic acid was added to the solution to decompose excess reducing reagent. The lyophilized sample was methanolyzed with 0.5 ml of 1.5N anhydrous methanolic hydrochloric acid at 90° C. for 4 hours. The methanolysate was evaporated in vacuo, and the residue was trimethylsilyated in pyridine with hexamethyldisilazane and trimethylsilyl chloride for 1 hour at room temperature. The column for gas-liquid chromatography was packed with 2% OV-17 on Chromosorb W, 80-100 mesh (0.5×300 cm). The temperature was programmed from 120° C. to 185° C. at the rate of 4° C. increment per min. Using maltose operated in the same manner as standard, the number of glucose of 1, 2, 3, 4 and 5 in each fraction were obtained from the molar ratio of glucose to glucitol. From this, the number of glucose units in the oligosaccharide of 3, 4, 5, 6 and 7 was determined (hereinafter referred to as "FG3, FG4, FG5, FG6 and FG7", respectively).

Since each modified oligosaccharide is not hydrolyzed by flucoamylase, it is possible to think that the modifying group (e.g. an aminopyridyl group) is introduced into a non-reducing end glucose unit. This was tested as follows.

Each fraction of FG3 to FG7 was methylated completely according to the Hakomori method [Lectures on Experiments in Biochemistry, vol. 4, Chemistry of Saccharides (the last volume), page 506, published by Tokyo Kagaku Dojin], hydrolyzed with an acid and identified by gas chromatography that methyl-2,3,4,6-tetra-O-methylgulcoside was not formed at all.

Further, each fraction of FG3 and FG5 was taken out and dissolved in a 0.1M sodium acetate buffer containing 10 mM calcium acetate buffer solution (pH 5.5), followed by addition of takaamylase A for hydrolyses at 37° C. for 3 hours. The hydrolyzed products were tested by HPLC and TLC. From FG5, there were produced FG3 and maltose, but FG3 was not hydrolyzed by takaamylase A. When FG3 was added to 0.3N HCl and hydrolyzed at 100° C. for 30 minutes, the products were maltose, glucose and 2 kinds of compounds having fluorescence but no maltotriose was produced.

EXAMPLE 2

Reagent (1) Reagent Solution (1)

In purified water, 100 mmole of sodium acetate, 10 mmole of calcium acetate, 0.36 mmole of maltopentaose having a 2-aminopyridyl group at the non-reducing end glucose unit prepared in Example 1 were dissolved, made pH 5.5 with sodium hydroxide and the total volume was made 1 liter.

Mearusing Procedures

To 500 μl of the reagent solution (1), 5 μl of serum was added and incubated at 37° C. for 15 minutes. The reaction solution was analyzed by HPLC and an amount of a modified oligosaccharide having 3 glucose units and 2-aminopyridyl group at the non-reducing end glucose unit was calculated from its peak area on chromatogram. On the other hand, a calibration curve was obtained by using standard samples having known α-amylase activity in the same manner as mentioned above. From this calibration curve, α-amylase activity of the serum was obtained.

Figure 1:
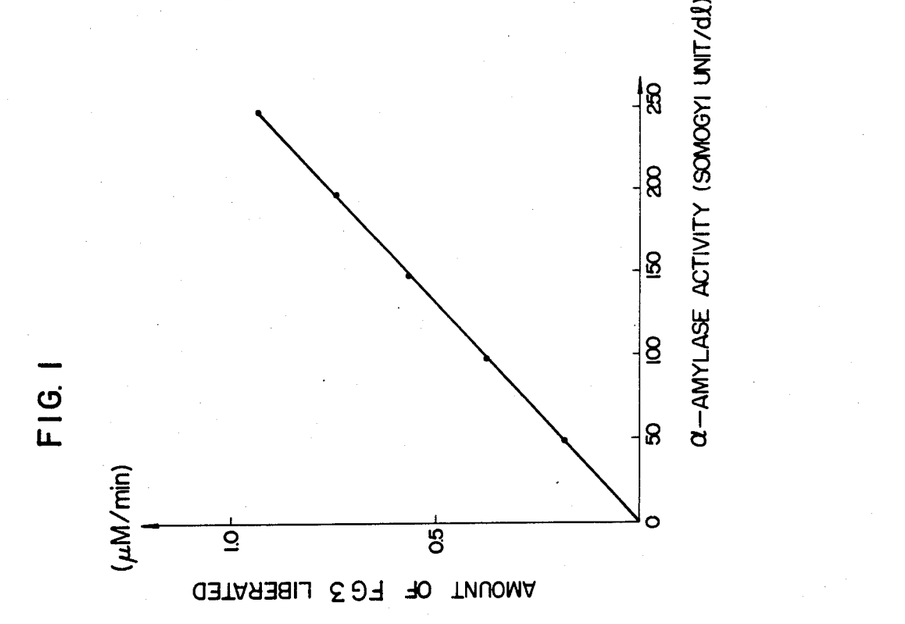
FIG. 1 is a calibration curve obtained in Example 2.

The relationship between α-amylase activity (Somogyi unit/dl) at each diluted stage of standard sample and the amount of FG3 liberated (μM) is shown in FIG. 1. The α-amylase activity of the standard sample was 200 Somogyi units.

The column of liquid chromatography was TSK-Gel LS 410, 5 μm, C18 (4×300 mm) (available from Toyo Soda Manufacturing Co., Ltd.), the eluate was 0.1M acetic acid solution containign 0.1% n-butanol and the effluent speed was 1.7 ml/min, the measuring temperature being room temperature.

EXAMPLE 3

Reagents (1) Reagent Solution (2)

40 mmole of Good's buffer solution (PIPES), 50,000 units of glucoamylase, 100,000 units of glucose oxidase, 200 units of mutarotase, 500,000 units of catalase, 0.7 mmole of 4-aminoantipyrine, 15 mmole of sodium chloride and 5 mmole of calcium chloride were dissolved in purified water, made pH 6.9 with sodium hydroxide and the total volume was made 1 liter.

(2) Reagent Solution (3)

In purified water, 40 mmole of Good's buffer solution (PIPES), 15,000 units of peroxidase, 15 mmole of sodium chloride, 5 mmole of calcium chloride, 3 g of maltopentaose having 2-aminopyridyl group at the non-reducing end glucose unit prepared in Example 1, 15 mmole of sodium azide and 10 mmole of phenol were dissolved, made pH 6.9 with sodium hydroxide and the total volume was made 1 liter

Measuring Procedures

To 2 ml of the reagent solution (2), 20 μl of a serum sample was added and incubated at 37° C. for 5 minutes. To this, 1 ml of the reagent solution (3) was added and reacted at 37° C. Changes of absorbance at 505 nm were measured for 3 minutes (ΔE/min) after 2 minutes to 5 minutes from the beginning of the reaction.

Figure 2:
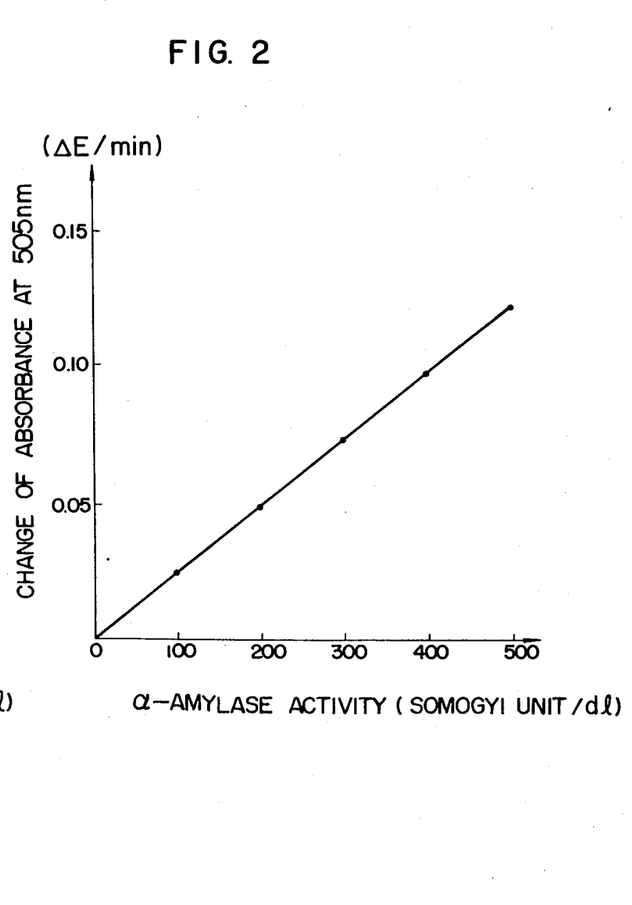
FIG. 2 is a calibration curve obtained in Example 3.

On the other hand, a calibration curve was obtained by using standard samples having known α-amylase activity in the same manner as mentioned above. From this calibration curve, α-amylase activity of the serum sample was obtained. The calibration curve used this time was shown in FIG. 2. The α-amylase activity in the standard sample was 500 Somogyi units.

EXAMPLE 4

Changes of absorbance of reagent blanks for 3 minutes were compared in the case of using maltohexaose having an aminopyridyl group as substrate with the case of using non-modified maltohexaose as substrate.

Reagents (1) Reagent Solution (4)

The same as the reagent solution (2) used in Example 3.

(2) Reagent Solution (5)

The same reagent solution (3) used in Example 3 except for using maltohexaose having an aminopyridyl group at the non-reducing end glucose unit in place of maltopentaose having an aminopyridyl group at the non-reducing end glucose unit was used.

(3) Reagent Solution (6)

The same reagent solution (3) used in Example 3 except for using non-modified maltohexaose in place of maltopentaose having an aminopyridyl group at the non-reducing end glucose unit was used.

Measuring Procedures

To 2 ml of the reagent solution (4), 20 μl of purified water was added and incubated at 37° C. for 5 minutes. To this 1 ml of the reagent solution (5) was added and reacted at 37° C. Changes of absorbance at 505 nm were measured for 3 minutes (ΔE/min) after 2 minutes to 5 minutes from the biginning of the reaction.

The same procedure as mentioned above was repeated except for using the reagent solution (6) in place of the reagent solution (5). The results are shown in Table 1.

TABLE 1

| Substrate | Change of absorbance of reagent blank for 3 minutes |
|---|---|
| Maltohexaose having aminopyridyl group | 0.006 |
| Maltohexaose | 0.0372 |

Using the modified oligosaccharides as substrate of this invention, it is also possible to separate and measure α-amylase isozymes, particularly α-amylase derived from human pancreas and α-amylase derived from human salivary glands. According to the special method of this invention, the measurement with high sensitivity becomes possible by using a very minute amount of sample. Further, according to the special process of this invention, an activity ratio of α-amylase derived from pancreas to α-amylase derived from salivary glands can be obtained by one time measurement.

The separation and measurement of α-amylase isozymes is based on the finding that reactivity of oligosaccharide derivatives changes depending on α-amylase isozymes. Further, when a special modifying group which can emit fluorescence or can show ultraviolet absorption is introduced into an oligosaccharide derivative, the resulting modified oligosaccharide can be effectively used as substrate for measuring α-amylase isozymes, the reaction products being able to be measured by a HPLC method easily.

In the separation and measurement of α-amylase isozymes, there are applied transglycosylation and hydrolysis reaction.

The following modified oligosacaharides of the formula (II) (having 5 glucose units) and the formula (III) (having 3 glucose units) can preferably be used as a substrate and acceptor.

In the above formula (II), $R_1$ is a modifying group which can emit fluorescence such as a 2-aminopyridyl or 3-aminopyridyl group or which can absorb ultraviolet light such as an anilino, methylanilino, hydroxyanilino, or carboxyphenylamino group. In the above formula (III), $R_2$ is also a modifying group which is the same as defined in $R_1$ and in addition which can be a hydroxyl group.

G: glucose unit.

The modified oligosaccharide of the formula (IV) can be represented in more detail as follows:

wherein $R_1$ and $R_2$ are as defined above.

The transglycosylation (6) is found for the first time by the present inventors.

The resulting oligosaccharide (IV) is subsequently hydrolyzed by α-amylase as shown by the equation (7).

In the above-mentioned reactions, the modified oligosaccharide (IV) having 6 glucose units is produced by the reaction (6), and the modified oligosaccharide having 4 glucose units and the modified oligosaccharide having 2 glucose units are produced from the modified oligosaccharide (VI) by the reaction (7). Generally speaking, in the reaction (6), there may naturally be produced oligosaccharide derivatives having glucose units of other than 6, while in the reaction (7), the oligosaccharide (VI) may be divided to those having 3 glucose units, respectively. The rates of hydrolysis is determined depending on the kind of α-amylase isozymes. Therefore, by selecting proper conditions under which the reaction is most different between α-amylase derived from pancreas and α-amylase derived from salivary glands, measurement of α-amylase isozymes becomes possible.

The modified oligosaccharides of the formulae (II) and (III) used as substrate for the transglycosylation (6) can be synthesized as follows, but not limited thereto.

SYNTHESIS EXAMPLE 1

Shynthesis of FG5

O-6-Deoxy-6-[(2-pyridyl)amino]-α-D-glucopyranosyl-(1→4)-O-α-D-glucopyranosyl-(1→4)-O-α-D-glucopyranosyl-(1→4)-O-α-D-glucopyranosyl-(1→4)-D-glucopyranose represented by the formula (II) was synthesized according to the process described in J. Biochem. Vol. 93, p 1055 (1983). That is, the primary alcohols at the 6-position of glucose units of dextrin were partially oxidized with dimethylsulfoxide and N,N'-dicyclohexylcarbodiimide, followed by formation of a Schiff's base with 2-aminopyridine and reduction with cyanoborohydride to form dextrin introducing 2-aminopyridyl group thereinto. On this, a liquefying type α-amylase derived from Bacillus subtilis and glucoamylase were acted to give a modified oligosaccharide introducing a 2-aminopyridyl group into the non-reducing end glucose unit, treated with gel filtration and freeze-drying of the objected fraction.

SYNTHESIS EXAMPLE 2

Synthesis of FG3

O-α-D-Glucopyranosyl-(1→4)-O-60-D-glucopyranosyl-(1→4)-1-deoxy-1-[(2-pyridyl)amino]-D-glucitol of the formula (III) was synthesized according to the reductive amination process described in J. Biochem. vol. 85, p. 217 (1979). That is, the aldehyde group at the 1-position of reducing end glucose unit of maltotriose was reacted with 2-aminopyridine to form a Schiff's base, which was then reduced. If necessary, the resulting product can be purified by HPLC.

The concentrations of the above-mentioned 2 kinds of substrates of the formulae (II) and (III) are preferably 50–200 μM/l for FG5 (II) and 1–10 mM/l for FG3 (III) in the reaction mixture. pH of the reaction mixture is generally 4 to 7, preferably 5 to 6.

In this invention, the whole of the substrates is reacted and the isozyme ratio can be obtained from the amount of a product. Therefore, if the product is measured previously using α-amylase isozyme standard solutions with known activity ratios, the isozyme ratio of serum sample can be obtained by measuring the amount of one of two products. Which product is to be measured can be selected by the easiness of determination and analytical conditions.

The separation and quantitative determination can be conducted by using HPLC.

In liquid chromatography, a gel permeation method, a reversed phase method or the like can effectively be used. Examples of conditions of liquid chromatography are as follows. In the case of the reversed phase chromatography, chemical bonding type silica gel introducing an alkyl group such as octadecylsilane, etc. is used as packing material. As the elution conditions, 0.1M ammonium acetate buffer solution, pH 3.0 to 4.5 containing 0.1 to 0.5% of n-butanol is excellent in separating ability. It is possible to measure at a flow speed of 1.5 to 2.0 ml/min, but not particularly limited thereto. The detection is usually conducted by either a fluorescence method or an ultraviolet method.

The 2-aminopyridyl group introduced as a substituent for applying to the detection in Synthesis Examples 1 and 2 emits fluorescence. Usually the wavelength of excitation and fluorescence are 320 nm and 400 nm, respectively.

According to this invention, activity ratios of α-amylase isozymes can be detected. If the total activity of α-amylases in the sample is obtained by a conventional method, activity values of individual isozymes can naturally be obtained by calculation.

Using as sample purified α-amylase derived from human salivary glands and purified α-amylase derived from human pancreas and as substrate the modified oligosaccharide of the formula (II) in which $R_1$ is 2-aminopyridyl and the modified oligosacchamide of the formula (III) in which $R_2$ is 2-aminopyridyl, the produced amount of oligosaccharide having 2 glucose units and having 2-aminopyridyl group at the reducing end is measured to find that the α-amylase derived from pancreas produced the product 6 times as large as that by the α-amylase derived from salivary glands.

It is also possible to measure α-amylase isozymes by only the hydrolysis reaction (7) using as substrate the modified oligosaccharide of the formula (IV) having 2-aminopyridyl at both the non-reducing and reducing ends, which is also a product of the transglycosylation (6). The modified oligosaccharide of the formula (IV) can be produced by, for example, Synthesis Example 3. Using said substrate, comparison of activities of α-amylase derived from human salivary glands and α-amylase derived from human pancreas becomes possible.

SYNTHESIS EXAMPLE 3

Synthesis of FG6

FG6 represented by the formula (IV) wherein both $R_1$ and $R_2$ are 2-aminopyridyl was synthesized according to the process described in J. Biochem. vol. 93, p. 1055 (1983). That is, the primary clcohols of the 6-position of glucose units of dextrin were partially oxidized with dimethylsulfoxide and N,N'-dicyclohexylcarbodiimide, folowed by formation of a Schiff's base with 2-aminopyridine and reduction with cyanoborohydride to form dextrin introducing 2-aminopyridyl group thereinto. On this, a liquefing type α-amylase derived from Bacillus subtilis and glucoamylase were acted to give a modified oligosaccharide introducing 2-aminopyridyl group into the non-reducing end glucose unit. After gel filtration, there was obtained a fraction of linear oligosaccharide having 6 glucose units, the non-reducing end unit of which has at the 6-position the primary alcohol substituted with 2-aminopyridyl. If necessary, the resulting product can be purified by HPLC.

SYNTHESIS EXAMPLE 4

Synthesis of FG6R

O-6-Deoxy-6-[(2-pyridyl)amino]-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucitol (FG6R) was synthesized according to the process described in J. Biochem. vol. 93, p.1055 (1983) and Method in Carbohydrate Chemistry II p.65–68 (1963). That is, the primary alcohols at the 6-position of glucose units of dextrin were partially oxidized with dimethylsulfoxide and N,N'-dicyclohexylcarbidiimide, followed by formation of a Schiff's base with 2-aminopyridine and reduction with cyanoborohydride to form dextrin introducing 2-aminopyridyl group thereinto. On this, a liquefying type α-amylase derived from Bacillus subtilis and glucoamylase were acted to give a modified oligosaccharide introducing 2-aminopyridyl group into the non-reducing end glucose unit. After gel filtration, this fraction was obtained by freeze-drying. In 1 ml of distilled water, 5 mg of the resulting modified oligosaccharide was dissolved. To the resulting solution, 2 ml of aqueous solution of 2.5 mg/ml of sodium borohydride was added and reacted at 4° C. for 18 hours to reduce the reducing end glucose unit to glucitol. Then, 100 μl of acetic acid was added to the reaction mixture to decompose excess sodium borohydride. After gel filtration, the fraction of O-6-deoxy-6-[(2-pyridyl)amino]-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucopyranosyl-(1→4)-D-glucitol was freeze-dried to give FG6R. If necessary, the resulting product can be purified by HPLC.

When the substrate FG6 or FG6R obtained by Synthesis Exaple 3 or 4 was actted on α-amylase derived from human salivary glands and α-amylase derived from human pancreas, it was admitted that α-amylase derived from human pancreas produced an oligosaccharide having 2 glucose units in an amount about 4 times as large as α-amylase derived from human salivary glands.

This means that only the hydrolysis reaction (7) of α-amylases makes it possible to measure α-amylase isozymes from the amounts of the products.

But the combination of the transglycosylation (6) and the hydrolysis reaction (7) is more preferable to give more accurate measurement of α-amylase isozymes as mentioned above.

The measurement of α-amylase isozymes can be conducted by using a very small amount of sample with high sensitivity. Further, activity ratios of α-amylase derived from pancreas and α-amylase derived from salivary glands in a sample can be obtained by one measurement.

The measurement of α-amylase isozymes is illustrated by way of the following Examples, but not limited thereto.

EXAMPLE 5

(a)

Preparation of Reagent Solution

[Reagent solution for measurement]

In 10 ml of 20 mM calcium acetate buffer solution (pH 5.5), 2.7 mg of modified oligosaccharide of the formula (V), 3.2 mg of modified oligosaccharide of the formula (VI) and 23.4 mg of sodium chloride were dissolved.

(b)

Preparation of Standard Solutions

A solution was prepared by dissolving 100 U of purified α-amylase derived from human salivary glands in 100 ml of 1 mM calcium chloride. On the other hand, a solution was prepared by dissolving 100 U of purified α-amylase derived from human pancreas in 100 ml of 1 mM calcium chloride. Three test tubes were numbered as Nos. 1, 2 and 3 and the above-mentioned solutions were mixed therein in amounts as listed in Table 2.

TABLE 2

| Test tube No. | α-Amylase solution derived from salivary glands, 100 U/dl (HSA) | α-Amylase solution derived from pancreas, 100 U/dl (HPA) | (HPA)/(HSA) (%) |
|---|---|---|---|
| 1 | 300 μl | 100 μl | 25 |
| 2 | 300 | 300 | 50 |
| 3 | 100 | 300 | 75 |

(c)

Measuring Procedures (1) α-Amylase Reaction

To 50 μl of individual standard solutions prepared or serum sample, 50 μl of the reagent solution for measurement was added in a test tube, mixed well and incubated at 37° C. for 3 hours.

(2) HPLC

The above-mentioned reaction solution in an amount of 10 μl was injected to HPLC. The amount of produced maltose derivative of the formula (VII) was calculated from the peak area.

Figure 3:
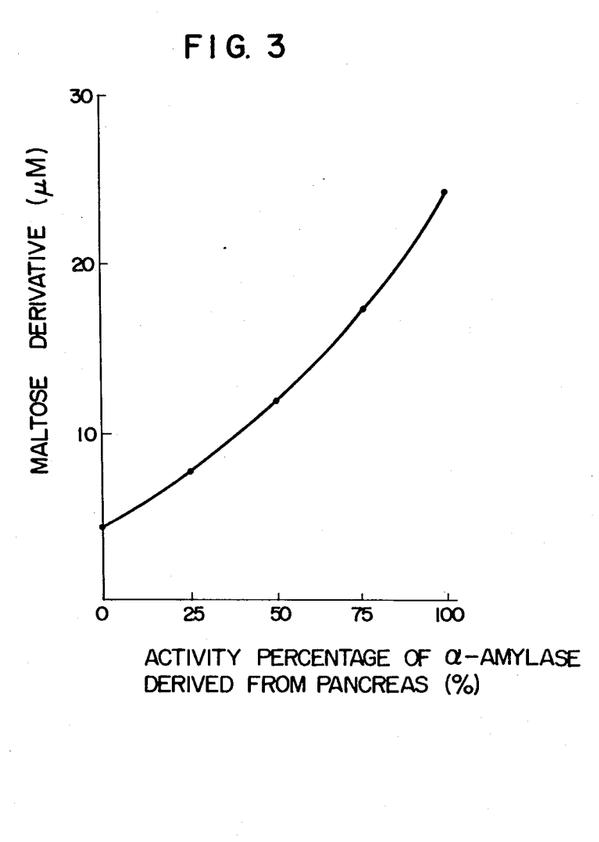
FIG. 3 is a calibration curve obtained in Example 5.

Measuring conditions of HPLC were as follows:
Column and packing material: A column (4×300 mm) packed with reversed phase type gel bonded with octadecylsilane (trade name: TSK Gel, LS-410, 5 μm, available from Toyo Soda Manufacturing Co., Ltd.)
Eluate: 0.1M ammonium acetate buffer solution containing 0.015% of n-butanol (pH 3.3)
Flow speed: 1.7 ml/min.
Detection: A fluorescence detector
  excitation wavelength 32 nm
  fluorescence wavelength 400 nm A calibration curve was obtained from the percentage of α-amylase derived from pancreas (HPA/HSA×100) and produced amount of the maltose derivative of the formula (VII) as shown in FIG. 3. On the other hand, the amount of the maltose derivative of the formula (VII) in the case of serum sample was obtained in the same manner as mentioned above. By using the calibration curve, the ratio of α-amylase isozymes was obtained.

Once the ratio of α-amylase derived from pancreas in the serum is obtained, activity values of α-amylase derived from pancreas and α-amylase derived from salivary glands can be calculated from total α-amylase activity values measured by a conventional method for measuring α-amylase activity.

EXAMPLE 6

(a)

Preparation of Reagent Solution

[Reagent solution for measurement]

In 20 ml of 20 mM calcium acetate buffer solution (pH 5.5), 2.2 mg modified oligosaccharide of the formula (VIII) and 30 mg of calcium chloride were dissolved.

(b)

Preparation of Standard Solutions

A solution was prepared by dissolving 100 U of purified α-amylase derived from human salivary glands in 100 ml of 1 mM calcium chloride. On the other hand, a solution was prepared by dissolving 100 U of purified α-amylase derived from human pancreas in 100 ml of 1 mM calcium chloride. Three test tubes were numbered as Nos. 1, 2 and 3 and the above-mentioned solutions were mixed therein in amounts as listed in Table 3.

TABLE 3

| Test tube No. | α-Amylase solution derived from salivary glands, 100 U/dl (HSA) | α-Amylase solution derived from pancreas, 100 U/dl (HPA) | (HPA)/(HSA) (%) |
|---|---|---|---|
| 1 | 300 μl | 100 μl | 25 |
| 2 | 300 | 300 | 50 |
| 3 | 100 | 300 | 75 |

(c)

Measuring Procedures (1) α-Amylase Reaction

To 50 μl of individual standard solutions prepared or serum sample, 50 μl of the reagent solution for measurement was added in a test tube, mixed well and incubated at 37°C. for 3 hours.

(2) HPLC

The above-mentioned reaction solution in an amount of 10 μl was injected to HPLC. The amount of produced maltose derivative of the formula (IX) was calculated from the peak area.

Figure 4:
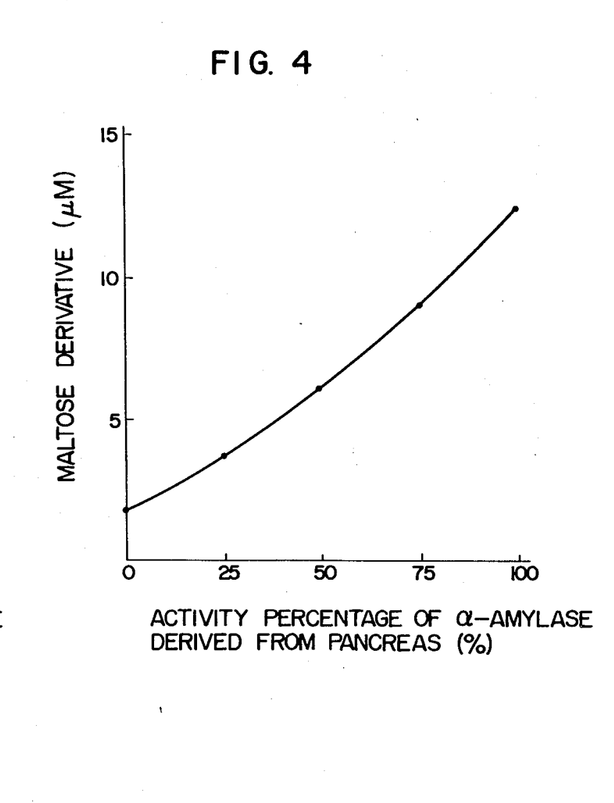
FIG. 4 is a calibration curve obtained in Example 6.

Measuring conditions of HPLC were as follows:
Column and packing material: A column (4×300 mm) packed with reversed phase type gel bonded with octadecylsilane (trade name: TSK Gel, LS-410, 5 μm, available from Toyo Soda Manufacturing Co., Ltd.)
Eluate: 0.1M ammonium acetate buffer solution containing 0.015% of n-butanol (pH 3.3)
Flow speed: 1.7 ml/min
Detection: A fluorescence detector
 excitation wavelength 320 nm
 fluorescence wavelength 400 nm A calibration curve was obtained from the percentage of α-amylase derived from pancreas (HPA/HSA×100) and produced amount of the maltose derivative of the formula (IX) as shown in FIG. 4. On the other hand, the amount of the maltose derivative of the formula (IX) in the case of serum sample was obtained in the same manner as mentioned above. By using the calibration curve, the ratio of α-amylase isozymes was obtained.

Once the ratio of α-amylase derived from pancreas in the serum is obtained, activity values of α-amylase derived from pancreas and α-amylase derived from salivary glands can be calculated from total α-amylase activity values measured by a conventional method for measuring α-amylase activity.

EXAMPLE 7

(a)

Preparation of Reagent Solution

[Reagent solution for measurement]

In 20 ml of 0.10M 3,3-dimethyl glutaric acid-sodium hydroxide buffer solution (pH 5.9) containing 10 mM sodium chloride and 5 mM calcium acetate, 2.5 mg of modified oligosaccharide of the formula (X) was dissolved.

(X)

(b)
Preparation of Standard Solutions

A solution was prepared by dissolving 100 U of purified α-amylase derived from human salivary glands in 100 ml of 1 mM calcium chloride. On the other hand, a solution was prepared by dissolving 100 U of purified α-amylase derived from human pancreas in 100 ml of 1

0.10M acetic acid was added thereto and heated at 100° C. for 10 minutes to stop the α-amylase reaction.

(2) HPLC

The above-mentioned reaction solution in an amount of 10 μl was injected to HPLC. The amounts of produced maltotriose derivative (FG3) of the formula (XI) and maltotetraose derivative (FG4) of the formula (XII) were calculated from the peak areas.

(XI)

(XII)

mM calcium chloride. Three test tubes were numbered as Nos. 1, 2 and 3 and the above-mentioned solutions were mixed therein in amounts as listed in Table 4.

TABLE 4

| Test tube No. | α-Amylase solution derived from salivary glands, 100 U/dl (HSA) | α-Amylase solution derived from pancreas, 100 U/dl (HPA) | (HPA)/(HSA) (%) |
|---|---|---|---|
| 1 | 300 μl | 100 μl | 25 |
| 2 | 300 | 300 | 50 |
| 3 | 100 | 300 | 75 |

(c)
Measuring Procedures (1) α-Amylase Reaction

To 15 μl of individual standard solutions prepared or serum sample, 30 μl of the reagent solution for measurement was added in a test tube, mixed well and incubated at 37° C. for 6 minutes. After the incubation, 0.3 ml of Measuring conditions of HPLC were as follows:

Column and packing material: A column (4×150 mm) packed with reserved phase type gel bonded with octadecylsilane (trade name: Cosmosil 5C$_{18}$, available from Nakarai Chemical, Ltd.)

Eluate: 0.10M ammonium buffer solution containing 0.05% 1-butanol (pH 3.3)

Flow speed: 2.0 ml/min.

Detection: A fluorescence detector
 excitation wavelength 320 nm
 fluorescence wavelength 400 nm

(d)
Calculation

Figure 5:
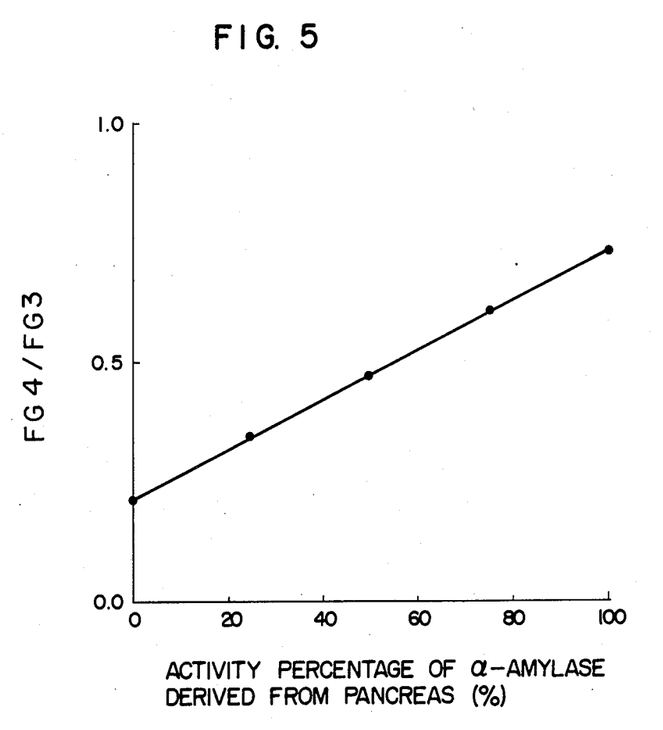
FIG. 5 is a calibration curve obtained in Example 7.

The ratio of produced amounts of FG4/FG3 obtained by HPLC is calculated. A calibration curve can be obtained from the relationship between the produced amount ratio of FG4/FG3 and the percentage of α-amylase derived from pancreas as shown in FIG. 5. On the other hand, the produced amount ratio of FG4/FG3 in the case of serum sample was obtained in the same manner as mentioned above. By using this calibration curve, the ratio of α-amylase derived from pancreas can be obtained.

Once the ratio of α-amylase derived from pancreas in the serum is obtained, the activity value of α-amylase derived from pancreas can be calculated from a total α-amylase activity value measured by a conventional method for measuring α-amylase activity.

What is claimed is:

1. A modified oligosaccharide represented by the formula:

(I)

wherein $R_1$ is a 2-aminopyridyl group, a 3-aminopyridyl group, an anilino group, a methylanilino group, a hydroxyanilino group or a carboxyphenylamino group; and n is an integer of 2 to 5.

2. A mixture of modified oligosaccharides represented by the formulae:

(II)

and (III)

wherein $R_1$ is a 2-aminopyridyl group, a 3-aminopyridyl group, an anilino group, a methylanilino group, a hydroxyanilino group or a carboxyphenylamino group; and $R_2$ is a 2-aminopyridyl group, a 3-aminopyridyl group, an anilino group, a methylanilino group, a hydroxyanilino group, a carboxyphenylamino group, or a hydroxyl group.

3. A modified oligosaccharide represented by the formula:

(IV)

wherein $R_1$ is a 2-aminopyridyl group, a 3-aminopyridyl group, an anilino group, a methylanilino group, a hydroxyanilino group or a carboxyphenylamino group; and $R_2$ is a 2-aminopyridyl group, a 3-aminopyridyl group, an anilino group, a methylanilino group, a hydroxyanilino group, a carboxyphenylamino group, or a hydroxyl group.

4. A modified oligasaccharide represented by the formula:

(III)

wherein $R_2$ is a 2-aminopyridyl group, a 3-aminopyridyl group, an anilino group, a methylanilino group, a hydroxyanilino group, a carboxyphenylamino group or a hydroxyl group.

* * * * *